(12) United States Patent
Ahn et al.

(10) Patent No.: US 11,566,059 B2
(45) Date of Patent: Jan. 31, 2023

(54) LONG-ACTING INSULIN ANALOGUES AND DERIVATIVES THEREOF

(71) Applicant: DAEWOONG PHARMACEUTICAL CO., LTD., Gyeonggi do (KR)

(72) Inventors: Kyong Hoon Ahn, Seoul (KR); Oh-Byung Kwon, Gyeonggi-do (KR); Seung Woo Kim, Gyeonggi-do (KR)

(73) Assignee: DAEWOONG PHARMACEUTICAL CO., LTD., Gyeonggi-Do (KR)

( * ) Notice: Subject to any disclaimer, the term of this patent is extended or adjusted under 35 U.S.C. 154(b) by 0 days.

(21) Appl. No.: 17/266,514

(22) PCT Filed: Jul. 18, 2019

(86) PCT No.: PCT/KR2019/008953
§ 371 (c)(1),
(2) Date: Feb. 5, 2021

(87) PCT Pub. No.: WO2020/032422
PCT Pub. Date: Feb. 13, 2020

(65) Prior Publication Data
US 2021/0300984 A1 Sep. 30, 2021

(30) Foreign Application Priority Data
Aug. 8, 2018 (KR) .................. 10-2018-0092243

(51) Int. Cl.
*C07K 14/62* (2006.01)
*A61K 38/00* (2006.01)
*C07K 1/14* (2006.01)

(52) U.S. Cl.
CPC ............ *C07K 14/62* (2013.01); *C07K 1/14* (2013.01); *A61K 38/00* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,750,497 A | 5/1998 | Havelund et al. | |
| 6,841,361 B1 | 1/2005 | Oka et al. | |
| 7,615,532 B2 | 11/2009 | Jonassen et al. | |
| 2011/0092419 A1 | 4/2011 | Nielsen et al. | |
| 2016/0289291 A1 | 10/2016 | Zimmerman et al. | |
| 2019/0142963 A1* | 5/2019 | Dimarchi ............ A61K 38/03 514/6.9 | |

FOREIGN PATENT DOCUMENTS

| | | |
|---|---|---|
| CN | 101541830 A | 9/2009 |
| EP | 0195691 A1 | 9/1986 |
| EP | 0368187 A2 | 11/1989 |
| KR | 1020120135123 A | 12/2012 |
| KR | 1020150058454 A | 5/2015 |
| KR | 1020150087130 A | 7/2015 |
| KR | 1020150138101 A | 12/2015 |
| RU | 2495131 C2 | 10/2013 |
| RU | 254150 C2 | 7/2014 |
| RU | 2524150 C2 | 7/2014 |
| WO | 2009115469 A1 | 9/2009 |
| WO | 2011161125 A1 | 12/2011 |
| WO | 2014048977 A1 | 4/2014 |

OTHER PUBLICATIONS

Katsoyannis, Journal of the Chem Soc., 1975 (5) 464-9 (Year: 1975).*
Wan, Biochem. (2005) 44, 5000-5016 (Year: 2005).*
Kurtzhals, P., et al., "Albumin binding of insulins acylated with fatty acids: characterization of the ligand-protein interaction and correlation between binding affinity and timing of the insulin effect in vivo", "Biochem. J.", 1995, pp. 725-731, vol. 312.
Chen, X.,, et al., "Fusion Protein Linkers: Property, Design, and Funcationality", Adv Drug Deliv Rev, 2014, pp. 1357-1369, vol. 65, No. 10, Publisher: NIH Public Access.
Dedova, I.I., "Insulin Therapy Manual for Doctors", Ministry of Health of the Russian Federation, 2004, Publisher: www.voed.ru/insulinotherapy.htm.
Dedova, I.I., "Insulin Therapy Manual for Doctors", Ministry of Health of the Russian Federation, 2004, Publisher: www.voed.ru/insulinotherapy.htm; English Translation.
Katsoyannis, P., et al., "A synthetic human insulin analogue modified at position B22. [Lys22-b] human insulin", Journal of the Chemical Society, Perkin Transactions 1, 1975, p. 1, vol. 5.
Maeda, Y., et al., "Engineering of Functional Chimeric Protein G-Vargula Luciferase", Analytical Biochemistry, 1997, pp. 147-152, vol. 249, No. AB972181, Publisher: Academic Press.
Orlando, M., "Modification of proeins and low molecular weight substances with hydroxyethyl starch (HES)", Biotechnologie-Gesellschaft Mittelhesen mbH, 2003, Publisher: Justus-Liebig-Universitat Giessen.

(Continued)

*Primary Examiner* — Thomas S Heard
(74) *Attorney, Agent, or Firm* — Hultquist, PLLC; Steven J. Hultquist

(57) ABSTRACT

The present invention relates to long-acting insulin analogues having an increased in vivo half-life in which the amino acid at position 22 of the B-chain of native insulin is substituted and one or more amino acids of the A-chain or B-chain of native insulin are additionally substituted, and to long-acting insulin analogue derivatives having a further increased in vivo half-life in which an albumin-binding domain is additionally fused to the long-acting insulin analogues. The insulin analogues or insulin analogue derivatives according to the present invention have a significantly increased in vivo half-life, and thus can provide convenience to diabetic patients who self-administer insulin by injection.

20 Claims, 7 Drawing Sheets
(6 of 7 Drawing Sheet(s) Filed in Color)
Specification includes a Sequence Listing.

(56) References Cited

OTHER PUBLICATIONS

Pakula, A., et al., "Genetic Analysis of Protein Stability and Function", Annu. Rev. Genet., 1898, pp. 289-310, vol. 23.

Schilling, RJ, et al., "Degradation of insulin by trypsin and alphachymotrypsin", Pharm Res., 1991, pp. 721-727, vol. 8, No. 6, Publisher: PubMed.

Tokuriki, N., et al., "Stability effects of mutations and protein evolvability", Structural Biology, 2009, pp. 596-604, vol. 19, Publisher: Elsevier.

Weitzel, G., et al., "Structure and activity of insulin, XV [1-5], Further evidence for the importance of arginine residue B22 in the activity of insulin. Semisyntheses of despentapeptide-(B23-30)-insulins varied in B22 using desnonapeptide (B22-30)-insulin and tetrapeptides", Chemistry Medicine, 1977, pp. DOI: 10.1515/BCHM2.1977.358.2.1573, Publisher: Semantic Scholar.

Zhou, J., et al., "Preparation and PEGylation of exedin-4 peptide secreted from yeast Pichia pastoris", European Journal of Pharmaceutics and Biopharmaceutics, 2009, pp. 412-417, vol. 72, Publisher: Elsevier.

Duttaroy, A., et al., "Development of a Long-Acting Insulin Analog Using Albumin Fusion Technology", Diabetes, Jan. 2005, vol. 54.

Mayer, J.P., et al., "Insulin Structure and Function", PeptideScience, 2007, pp. 687-713, vol. 88, No. 5, Publisher: Wiley InterScience.

\* cited by examiner

LONG-ACTING INSULIN ANALOGUES AND DERIVATIVES THEREOF

CROSS-REFERENCE TO RELATED APPLICATIONS

This application is a U.S. national phase under 35 USC § 371 of International Patent Application No. PCT/KR2019/008953 filed Jul. 19, 2019, which in turn claims priority under 35 USC § 119 of Korean Patent Application No. 10-2018-0092243 filed Aug. 8, 2018. The disclosures of International Patent Application No. PCT/KR2019/008953 and Korean Patent Application No. 10-2018-0092243 are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "553_UpdatedSeqListing_ST25.txt" created on Mar. 4, 2022 and is 8,041 bytes in size. The sequence listing contained in this .txt file is part of the specification and is hereby incorporated by reference herein in its entirety.

TECHNICAL FIELD

The present invention relates to long-acting insulin analogues and derivatives thereof, and more particularly to long-acting insulin analogues having an increased in vivo half-life in which the amino acid at position 22 of the B-chain of native insulin is substituted and one or more amino acids of the A-chain or B-chain of native insulin are additionally substituted, and to long-acting insulin analogue derivatives having a further increased in vivo half-life in which an albumin-binding domain is additionally fused to the long-acting insulin analogues.

BACKGROUND ART

Diabetes is a metabolic disease characterized by high glucose levels, and is developed by a combination of genetic and environmental factors. Diabetes includes type 1 diabetes, type 2 diabetes, gestational diabetes, and other states that cause hyperglycemia. Diabetes means a metabolic disorder in which the pancreas produces insufficient amounts of insulin or in which the human body's cells fail to respond appropriately to insulin, and thus their ability to absorb glucose is impaired. As a result, glucose builds up in the blood.

Type 1 diabetes, also called insulin-dependent diabetes mellitus (IDDM) and adolescent-onset diabetes, is caused by beta-cell destruction, leading to absolute insulin deficiency. On the other hand, type 2 diabetes, known as non-insulin dependent diabetes mellitus (NIDDM) and adult-onset diabetes, is associated with predominant insulin resistance and thus relative insulin deficiency and/or a predominantly insulin secretory defect with insulin resistance.

In particular, diabetes is associated with various complications such as cardiovascular disease and retinopathy, and thus is a disease that becomes very burdensome if proper management such as blood glucose control is not done. The world market for diabetes medications is expected to expand from $41.7 billion in 2015 to $66.1 billion by 2022, and is expected to be the second largest after the anticancer drug market. Globally, there are 422 million adults with diabetes in 2014, which is 8.5% of the total adult population, nearly double that of 4.5% in 1980 (WHO, 2016). In addition, the total global health expenditure due to diabetes is estimated at $673 billion, and the number of diabetic patients aged 20-79 is expected to increase to about 620 million by 2040.

The most representative treatment methods for treating diabetes include a method of administering insulin to control the blood glucose level of the patient to a normal level. Insulin is a blood glucose-regulating hormone that is secreted from the human pancreas. It functions to transfer excess glucose in the blood to cells to supply energy to the cells and maintain the blood glucose levels at normal levels.

As the recombinant protein manufacturing technology has been developed, a variety of insulin products have been put on the market. Insulin products can be broadly classified into five types according to their action. Among these, rapid-acting insulin, which exhibits the fastest action, is characterized in that it shows rapid efficacy, begins to act between 1 minute and 20 minutes, and shows the highest efficacy after about 1 hour, and its efficacy lasts for 3 to 5 hours. Representative rapid-acting products include insulin aspart (NovoRapid®), insulin lispro (Humalog®), and insulin glulisine (Apidra®). Insulin, which shows the second fastest action, is regular insulin. The regular insulin begins to lower blood glucose levels at 30 minutes after administration, and shows the highest efficacy between 2 to 4 hours, and its efficacy lasts for 6 to 8 hours. Representative regular insulin products include Actrapid®, Humilin® R, Hypurin Neutral and the like. Intermediate-acting insulin is a substance obtained by adding protamine or zinc to delay its action. This insulin begins to act from about 1 hour and 30 minutes after injection, and the efficacy thereof reaches the highest level between 4 hours and 12 hours and lasts for 16 to 24 hours. Representative intermediate-acting products include Protaphane®, Humulin® NPH, and Hypurin Isophane®. Premixed insulin is obtained by premixing rapid-acting insulin or regular insulin with intermediate-acting insulin so that the two kinds of insulin can be easily administered by single injection. Commercially available premixed insulin products include NovoMix® 30 (30% insulin aspart and 70% protamine crystalline insulin aspart), Humalog®Mix 25 (25% insulin lispro and 75% insulin lispro protamine suspension), and Humalog®Mix 50 (50% insulin lispro and 50% insulin lispro protamine suspension). Finally, long-acting insulin is injected once or twice a day, and its efficacy lasts for up to 24 hours. It is usually used as basal insulin, and commercially available long-acting insulin products include Lantus® (insulin glargine, EP 0368187), Levemir® (insulin detemir, U.S. Pat. No. 5,750,497), and Tresiba® (insulin degludec, U.S. Pat. No. 7,615,532).

Insulin is used in different applications depending on its action. For type 1 diabetes, long-acting insulin needs to be administered in addition to regular or rapid-acting insulin, and for type 2 diabetes that requires insulin therapy, regular or rapid-acting insulin may be administered together with long-acting insulin, or only long-acting insulin may also be administered.

As described above, insulin administration is the most representative treatment method for treating diabetes. However, long-acting insulins are inconvenient in that they need to be administered once or twice daily, because the half-lives thereof are not yet sufficiently long. This causes discomfort to diabetic patients who self-administer insulin by injection.

Currently commercially basal insulin products are mostly daily formulations, and there are no product having improved convenience of administration compared to these products. Novo Nordisk developed an insulin analogue (US No. 2011/0092419A1) having an increased in vivo half-life by introducing a mutation into the insulin sequence so as to have resistance to proteases in vivo, and also developed an insulin having an additionally increased half-life through acylation of the insulin analogue (WO2009/115469, WO2011/161125), but this insulin may be used as a daily formulation. Hanmi Pharmaceuticals developed insulin having an increased half-life by conjugation a Fc region to an insulin analogue (KR 10-2015-0087130). However, a method for producing the insulin developed by Hanmi Pharmaceuticals is complicated, because insulin and Fc are produced separately and subjected to PEGylation.

Thus, the present invention is intended to overcome the above-described problems, in order to minimize inconvenience which occurs when the number of injections is large in the use of conventional basal insulin, develop insulin of which action time is extended, and also improve its production method.

Albumin is the most abundant protein in blood, and has effects on the in vivo pharmacokinetics of many drugs, and thus many studies have been conducted to control the binding affinity of drugs for albumin in new drug development. For example, for the development of long-acting insulin, Novo Nordisk developed a product (insulin detemir, insulin degludec), which can be absorbed from subcutaneous tissue (site of administration) into the blood at reduced rate, by acylation of insulin with a fatty acid having a binding affinity for albumin. The binding affinity of fatty acids for albumin shows a high correlation with the absorption rate of insulin. When a fatty acid having a high binding affinity for albumin is acylated to insulin, the half-life of the insulin is increased. For example, insulin detemir binds to albumin in blood, thus increasing its half-life. When human insulin was administered intravenously, it had a half-life of 2.4 minutes, whereas insulin detemir had a half-life of 18 to 25 minutes, which was at least 10-fold longer. Insulin degludec had a 2.4-fold increased binding affinity for albumin compared to insulin detemir, and thus had an increased half-life.

However, acylated insulin has a binding affinity ($K_d$) of several mM (Biochem. J. 312, 725-731 (1995)) for albumin, and thus does not have improved pharmacokinetic profiles compared to daily formulations. Accordingly, the present invention is intended to maximize the half-life extending effect of albumin by using an albumin-binding domain (ABD) whose binding affinity for albumin reaches pM levels.

Accordingly, the present inventors have made extensive efforts to develop long-acting insulin having improved lasting time which overcomes the inconvenience of frequent insulin administration to diabetic patients, and as a result, have found that an insulin analogue derivative obtained by substituting one or more amino acids of the A-chain and B-chain of native insulin and additionally fusing an albumin-binding domain has a significantly increased in vivo half-life, thereby completing the present invention.

DISCLOSURE OF INVENTION

Technical Problem

It is an object of the present invention to provide a novel insulin analogue that shows a resistance to cleavage by enzyme clostripain as well as an increased in vivo half-life, a nucleotide encoding the analogue, a vector comprising the nucleotide, and a recombinant microorganism having introduced therein the vector.

Another object of the present invention is to provide a novel insulin analogue derivative that shows a resistance to cleavage by enzyme clostripain as well as an increased in vivo half-life, a nucleotide encoding the analogue derivative, a vector comprising the nucleotide, and a recombinant microorganism having introduced therein the vector.

Still another object of the present invention is to provide a method for producing an active form of a long-acting insulin analogue derivative having an increased in vivo half-life.

Technical Solution

To achieve the above object, the present invention provides an insulin analogue comprising an insulin B-chain variant represented by the amino acid sequence of SEQ ID NO: 2, arginine (Arg) at amino acid position 22 of an insulin B-chain is substituted with lysine (Lys) in native insulin.

The present invention also provides a polynucleotide encoding the insulin analogue.

The present invention also provides a recombinant vector comprising the polynucleotide.

The present invention also provides a recombinant microorganism having introduced therein the recombinant vector.

The present invention also provides a long-acting insulin analogue derivative in which an albumin-binding domain is fused to the insulin analogue.

The present invention also provides a recombinant vector that comprises a polynucleotide encoding the insulin analogue and a polynucleotide encoding an albumin-binding domain comprising an albumin-binding motif represented by the following amino acid sequence:

GVSDFYKKLIX$_a$KAKTVEGVEALKX$_b$X$_c$I (SEQ ID NO: 14)

Wherein
X$_a$ is independently selected from D and E,
X$_b$ is independently selected from D and E, and
X$_c$ is independently selected from A and E.

The present invention also provides a recombinant microorganism having introduced therein the recombinant vector.

The present invention also provides a method for producing an active form of a long-acting insulin analogue derivative having an increased in vivo half-life, the method comprising the steps of: (a) culturing the recombinant microorganism; (b) lysing the cultured recombinant microorganism, thereby obtaining a long-acting insulin analogue derivative; (c) inducing refolding of the obtained long-acting insulin analogue derivative, thereby obtaining a pre-pro form of an insulin analogue derivative; (d) converting the pre-pro form of the insulin analogue derivative to an active form by treating with clostripain and CpB; and (e) purifying the active form of the long-acting insulin analogue derivative.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
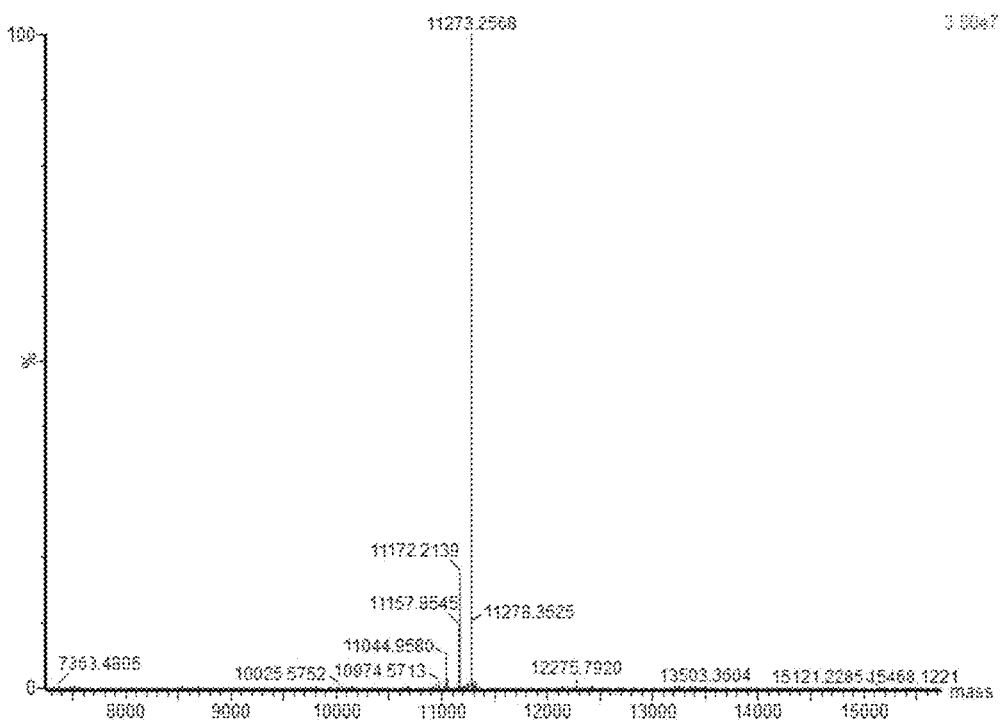
FIG. 1 shows the results of analyzing the stability of an ABD-fused insulin analogue constructed by substituting arginine (Arg) at position 22 of the insulin B-chain with lysine (Lys) by treating with clostripain. Mass spectrometry indicated that when the insulin B-chain contained arginine (Arg) at position 22, cleavage thereof occurred, but when the arginine (Arg) was substituted with lysine (Lys), cleavage of the B-chain did not occur.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, it has been found that an insulin analogue, in which the amino acid arginine (Arg) at position 22 of the B-chain of native insulin is substituted from arginine (Arg) to lysine (Lys) and one or more amino acids of the A-chain or B-chain of native insulin are additionally substituted, has an increased in vivo half-life and, at the same time, can be easily produced using a microorganism. In addition, it has been found that when an albumin-binding domain is additionally fused to the insulin analogue, the in vivo half-life of the insulin analogue can further be increased.

The present invention includes an insulin-ABD fusion protein having a significantly increased half-life in which an albumin-binding domain (ABD) having a high binding affinity for albumin is fused to native insulin so that the rate of absorption of the insulin into blood can be reduced and so that the stability of the insulin in blood can be increased. In addition, the present invention includes an insulin analogue in which the amino acid arginine (Arg) at position 22 of the B-chain of native insulin is substituted from arginine (Arg) to lysine (Lys) and/or one or more amino acids of the A-chain or B-chain of native insulin are substituted, thereby minimizing protease cleavage or insulin receptor-mediated removal. Also, the present invention includes insulin analogue-ABD fusion protein in which the said various insulin analogue is fused to albumin-binding domain (ABD). This fusion protein retains the insulin's intrinsic property of forming a hexamer, and thus can be used in formulation development and makes it possible to improve absorption rate.

Therefore, in one aspect, the present invention is directed to an insulin analogue comprising an insulin B-chain variant represented by the amino acid sequence of SEQ ID NO: 2, arginine (Arg) at amino acid position 22 of an insulin B-chain is substituted with lysine (Lys) in native insulin. According to the present invention, when the amino acid at position 22 of the insulin B-chain is substituted from arginine (Arg) to lysine (Lys), the insulin analogue may show a resistance to cleavage by enzyme clostripain, making it possible to convert the insulin to an active form by the enzyme clostripain other than trypsin in a process of producing the insulin analogue in microorganisms or cells other than the human body.

In the present invention, "an insulin analogue comprising an insulin-B chain variant represented by the amino acid sequence of SEQ ID NO: 2, arginine (Arg) at amino acid position 22 of an insulin-B chain is substituted with lysine (Lys) in native insulin" means that the insulin analogue may comprise further amino acid variant in insulin A chain or insulin B chain in addition to arginine (Arg)_-to-lysine (Lys) substitution at amino acid position 22 of an native insulin B chain.

In the present invention, the insulin analogue may further comprise one or more amino acid substitutions selected from the group consisting of: (i) a valine (Val)-to-leucine (Leu) substitution at amino acid position 3 of an insulin A-chain represented by the amino acid sequence of SEQ ID NO: 4; (ii) a threonine (Thr)-to-aspartic acid (Asp) substitution at amino acid position 8 of the insulin A-chain represented by the amino acid sequence of SEQ ID NO: 4; (iii) an isoleucine (Ile)-to-lysine (Lys) substitution at amino acid position 10 of the insulin A-chain represented by the amino acid sequence of SEQ ID NO: 4; (iv) a tyrosine (Tyr)-to-glutamic acid (Glu) substitution at amino acid position 14 of the insulin A-chain represented by the amino acid sequence of SEQ ID NO: 4; (v) a tyrosine (Tyr)-to-phenylalanine (Phe) substitution at amino acid position 19 of the insulin A-chain represented by the amino acid sequence of SEQ ID NO: 4; (vi) a histidine (His)-to-threonine (Thr) substitution at amino acid position 5 of an insulin B-chain variant represented by the amino acid sequence of SEQ ID NO: 2; (vii) a serine (Ser)-to-aspartic acid (Asp) substitution at amino acid position 9 of the insulin B-chain variant represented by the amino acid sequence of SEQ ID NO: 2; (viii) a glutamic acid (Glu)-to-alanine (Ala) substitution at amino acid position 13 of the insulin B-chain variant represented by the amino acid sequence of SEQ ID NO: 2; (ix) a leucine (Leu)-to-glutamine (Gln) substitution at amino acid position 17 of the insulin B-chain variant represented by the amino acid sequence of SEQ ID NO: 2; and (x) a phenylalanine (Phe)-to-serine (Ser) substitution at amino acid position 24 of the insulin B-chain variant represented by the amino acid sequence of SEQ ID NO: 2, but is not limited thereto.

In the present invention, the insulin analogue may have an increased in vivo half-life compared to native insulin. The in vivo half-life may last for preferably at least 48 hours, more preferably at least 72 hours.

In another aspect, the present invention is directed to a polynucleotide encoding the insulin analogue. In still another aspect, the present invention is directed to a recombinant vector comprising the polynucleotide. In yet another aspect, the present invention is directed to a recombinant microorganism having introduced therein the recombinant vector.

Meanwhile, the present invention is directed to a long-acting insulin analogue derivative wherein an albumin-binding domain is fused to the insulin analogue. The long-acting insulin analogue derivative fused with an albumin-binding domain has a comparatively high affinity for albumin.

In an example of the present invention, the albumin-binding domain may comprise an albumin-binding motif represented by the following amino acid sequence:

```
GVSDFYKKLIX_aKAKTVEGVEALKX_bX_cI (SEQ ID NO: 14)
``` wherein
$X_a$ is independently selected from D and E,
$X_b$ is independently selected from D and E, and
$X_c$ is independently selected from A and E.

In an example of the present invention, $X_a$ is D, $X_b$ is D, and $X_c$ is A.

In an embodiment of the present invention, the albumin-binding domain may comprise the following amino acid sequence:

```
LAX_3AKX_6X_7ANX_10ELDX_14Y-[BM]-LX_43X_44LP (SEQ ID NO: 15)
``` wherein
[BM] is the albumin-binding motif as defined in the foregoing paragraph (SEQ ID NO: 14),
$X_3$ is independently selected from C, E, Q, and S;
$X_6$ is independently selected from C, E, and S;
$X_7$ is independently selected from A and S;
$X_{10}$ is independently selected from A, R, and S;
$X_{14}$ is independently selected from A, C, K, and S;
$X_{43}$ is independently selected from A and K; and
$X_{44}$ is independently selected from A, E, and S.

The albumin-binding domain may be represented by the amino acid sequences selected from the group consisting of SEQ ID NOS: 6 to 13, is not limited thereto. The albumin-binding domain may preferably be represented by an amino acid sequence of SEQ ID NO: 6.

In the present invention, it is preferable that the albumin binding domain is fused to C-terminus of A-chain in insulin or insulin analogue of B-chain-C-chain-A-chain in terms of protein refolding efficiency, enzyme reaction efficiency and activity of the produced insulin derivative or insulin analogue derivatives. In this, a linker may be introduced between the insulin (or insulin analogue) and the albumin binding domain.

The function of the long-acting insulin analogue derivative according to the present invention varies depending on the three-dimensional structure of the derivative. Thus, it is possible to make small changes in the amino acid sequence of the long-acting insulin analogue derivative according to the present invention without affecting the function of the derivative. Therefore, the present invention includes variants of the albumin-binding domain or the long-acting insulin analogue derivative, which retain an albumin binding property or high resistance to enzymatic cleavage. For example, amino acid residues belonging to a specific functional group of amino acid residues (e.g., hydrophobicity, hydrophilicity, polarity, etc.) may be replaced with other amino acid residues belonging to the same functional group.

As used herein, the terms "albumin binding" and "binding affinity for albumin" refer to the property of a polypeptide or protein which may be tested by the use of surface plasmon resonance technology, such as a Biacore instrument. For example, albumin binding affinity may be tested in an experiment in which albumin or a fragment of thereof is immobilized on a sensor chip of the instrument, and a sample containing a polypeptide or protein to be tested is passed over the chip.

Alternatively, a polypeptide or protein to be tested is immobilized on a sensor chip of the instrument, and a sample containing albumin or a fragment thereof is passed over the chip. In this regard, the albumin may be serum albumin of mammalian origin, such as human serum albumin. Those skilled in the art may interpret the results obtained by such experiments to establish a quantitative measure of the binding affinity of the polypeptide or protein for albumin. If a quantitative measure is desired, for example to determine a $K_D$ value for the interaction, surface plasmon resonance methods may also be used. Binding values may for example be defined in a Biacore 2000 instrument (Biacore AB). Albumin is suitably immobilized on a measurement sensor chip, and samples of a polypeptide or protein whose affinity is to be determined are prepared by serial dilution and injected in random order. $K_D$ values may then be calculated from the results using, for example, the 1:1 Langmuir binding model of the BIAevaluation 4.1 software provided by the instrument manufacturer.

In one embodiment of the present invention, albumin to which the long-acting insulin analogue derivative binds may be selected from among human serum albumin, rat serum albumin, cynomolgus serum albumin, and mouse serum albumin, but is not limited thereto.

In one specific embodiment, albumin to which the long-acting insulin analogue derivative binds is human serum albumin.

The insulin analogue and the albumin-binding domain are linked to each other by a peptide bond; a polypeptide linker; or a non-peptidyl linker selected from the group consisting of polyethylene glycol, polypropylene glycol, an ethylene glycol-propylene glycol copolymer, polyoxyethylated polyol, polyvinyl alcohol, polysaccharides, dextran, polyvinyl ethyl ether, biodegradable polymers, fatty acids, nucleotides, lipid polymers, chitin, hyaluronic acid, and combinations thereof, but are not limited thereto.

In the present invention, a linker consisting of a repeat of a $(GGGGS)_n$ (wherein n is an integer ranging from 1 to 6) sequence (SEQ ID NO: 16) may be inserted between the insulin analogue and the albumin-binding domain. This is based on experimental results indicating that when the linker was not introduced, the refolding yield was low, but when two or more repeats of the (GGGGS) sequence (SEQ ID NO: 16) were introduced, there was no significant difference in the refolding yield. Meanwhile, as the number (n) of repeats of the sequence increased, the rate of conversion to an active form of insulin by clostripain increased, but the in vivo pharmacokinetics of the insulin analogue was not significantly influenced. Taking the above-described results together, the linker preferably consists of 2 to 4 repeats of the GGGGS (SEQ ID NO: 16) sequence.

Therefore, in the present invention, the insulin analogue and the albumin-binding domain can be linked to each other by the polypeptide linker, and the polypeptide linker may comprise $(GGGGS)_n$ (wherein n is an integer ranging from 1 to 6) (SEQ ID NO: 16), but is not limited thereto. Preferably, the polypeptide linker may be represented by an amino acid sequence of SEQ ID NO: 5.

In a still further aspect, the present invention is directed to a recombinant vector that comprises: a polynucleotide encoding the insulin analogue; and a polynucleotide encoding an albumin-binding domain comprising an albumin-binding motif represented by the following amino acid sequence:

GVSDFYKKLIX$_a$KAKTVEGVEALKX$_b$X$_c$I (SEQ ID NO: 14)

Wherein
X$_a$ is independently selected from D and E,
X$_b$ is independently selected from D and E, and
X$_c$ is independently selected from A and E.

In an embodiment of the present invention, the albumin-binding domain may comprise the following amino acid sequence:

LAX$_3$AKX$_6$X$_7$ANX$_{10}$ELDX$_{14}$Y-[BM]-LX$_{43}$X$_{44}$LP (SEQ ID NO: 15)

wherein
[BM] is the albumin-binding motif as defined in the foregoing paragraph (SEQ ID NO: 14),
X$_3$ is independently selected from C, E, Q, and S;
X$_6$ is independently selected from C, E, and S;
X$_7$ is independently selected from A and S;
X$_{10}$ is independently selected from A, R, and S;
X$_{14}$ is independently selected from A, C, K, and S;
X$_{43}$ is independently selected from A and K; and
X$_{44}$ is independently selected from A, E, and S.

The albumin-binding domain may be represented by the amino acid sequences selected from the group consisting of SEQ ID NOS: 6 to 13, but is not limited thereto. The albumin-binding domain may preferably be represented by an amino acid sequence of SEQ ID NO: 6.

In the present invention, the polynucleotide encoding the insulin analogue and the nucleotide encoding the albumin binding domain may be introduced into the recombinant vector so that the insulin analogue and the albumin binding domain can be expressed as a fusion protein.

The other description of the albumin-binding domain introduced into the recombinant vector overlaps with the description of the albumin-binding domain of the long-acting insulin analogue derivative, and thus is omitted. In addition, a polynucleotide encoding the polypeptide linker may be included between a polynucleotide encoding the insulin analogue and a polynucleotide encoding the albumin-binding domain. The description of the polypeptide linker also overlaps with the description of the polypeptide linker of the long-acting insulin analogue derivative, and thus a detailed description thereof will be omitted to avoid redundancy.

In the meantime, the description of the albumin-binding motif and the albumin-binding domain (or albumin-binding polypeptide) is construed to include the content disclosed in Korean Patent Laid-Open Publication No. 10-2015-0058454 corresponding to WO 2014048977.

The recombinant vector according to the present invention may be constructed as a vector for conventional cloning or expression, and may be constructed as a vector to use in a prokaryotic or eukaryotic cell as a host cell.

As used herein, the term "vector" refers to a recombinant vector capable of expressing a target protein in an appropriate host cell, which is a gene construct including essential regulatory factors operably linked to enable the expression of a nucleic acid insert. The present invention can prepare a recombinant vector which includes a nucleic acid encoding an insulin analogue and/or analogue derivative thereof. The insulin analogue and/or analogue derivative thereof of the present invention may be produced in a recombinant microorganism into which the recombinant vector is introduced by transformation or transfection, by lysing and purifying the cultured recombinant microorganism.

In the present invention, the nucleic acid encoding the insulin analogue and analogue derivative thereof is operably linked to a nucleic acid expression control sequence. As used herein, the term "operably linked" refers to a functional linkage between a nucleic acid expression control sequence (e.g., a promoter, a signal sequence, a ribosome-binding site, a transcription termination sequence, etc.) and another nucleotide sequence, and thus the control sequence can control the transcription and/or translation of the nucleotide sequence.

As used herein, the term "promoter" refers to an untranslated nucleic acid sequence located upstream of a coding region, which includes a polymerase-binding site and has the activity of initiating transcription of a gene located downstream of the promoter into mRNA, i.e., a DNA site to which polymerase binds and initiates the transcription of a gene, and it is located at the 5' region of mRNA transcription initiation region.

For example, when the vector of the present invention is a recombinant vector, and a prokaryotic cell is used as a host cell, a strong promoter capable of promoting transcription (such as tac promoter, lac promoter, lacUV5 promoter, lpp promoter, pLλ promoter, pRλ promoter, rac5 promoter, amp promoter, recA promoter, SP6 promoter, trp promoter, trc promoter, phoA promoter, araBAD promoter, T5 promoter, and T7 promoter), a ribosome-binding site for initiation of translation, and a transcription/translation termination sequences are generally included.

Additionally, a vector that can be used in the present invention may be prepared by manipulating plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4λB, λ-Charon, λΔz1, M13, etc.), or viruses (e.g., SV40, etc.), which are commonly used in the art, but is not limited thereto.

Meanwhile, when the vector of the present invention is a recombinant vector, and a eukaryotic cell is used as a host cell, promoters derived from the genomes of mammalian cells (e.g., metallothionein promoter), promoters derived from mammalian viruses (e.g., adenovirus late promoter, 7.5K promoter of vaccinia virus, SV40 promoter, cytomegalovirus promoter, and tk promoter of HSV) may be used, and in general, the vector includes a polyadenylated sequence (e.g., a bovine growth hormone terminator and a polyadenylated sequence derived from SV40) as a transcription termination sequence.

In addition, the recombinant vector of the present invention includes an antibiotic resistance gene commonly used in the art as a selective marker, and may include, for example, genes having resistance to ampicillin, gentamicin, carbenicillin, chloramphenicol, streptomycin, kanamycin, geneticin, neomycin, or tetracycline.

The recombinant vector of the present invention may additionally include a different sequence to make it easy to purify target proteins being recovered, i.e., insulin analogue and/or insulin analogue derivative. The sequence to be additionally included may be a tag sequence for protein purification, e.g., glutathione S-transferase (Pharmacia, USA), a maltose-binding protein (NEB, USA), FLAG (IBI, USA), 6-histidine, etc., but the kinds of the sequence necessary for the purification of target proteins are not limited thereto. Fusion proteins expressed by the recombinant vector including the above tag sequence may be purified by affinity chromatography. For example, when glutathione S-transferase is fused, glutathione, which is the substrate of the enzyme, may be used, and when 6-histidine tag is used, a desired target protein may be easily collected by a Ni-NTA column. A recombinant microorganism transformed with the vector can be constructed using a recombinant vector comprising a polynucleotide encoding the insulin analogue and/or insulin analogue derivative.

As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, the Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation method, a transformation method using PEG, dextran sulfate-, lipofectamine-, and dry/suppression-mediated transformations, etc.

The method for transforming the recombinant vector including a nucleic acid encoding an insulin analogue and/or insulin analogue derivative according to the present invention may not be limited to these methods, but any method for transformation or transfection commonly used in the art may be used without limitation.

A recombinant transformant of the present invention may be obtained by introducing a recombinant vector including a nucleic acid encoding an insulin analogue and/or insulin analogue derivative into a host cell.

An appropriate host to be used in the present invention may not be particularly limited as long as it can express the nucleic acid of the present invention. Examples of the appropriate host may include a bacteria belonging to the genus *Escherichia* such as *E. coli*, a bacteria belonging to the genus *Bacillus* such as *Bacillus subtilis*, a bacteria belonging to the genus *Pseudomonas* such as *Pseudomonas putida*, yeasts such as *Pichia pastoris, Saccharomyces cerevisiae,* and *Schizosaccharomyces pombe,* an insect cell such as *Spodoptera frugiperda* (SF9), and animal cells such as CHO, COS, and BSC, but is not limited thereto.

The present invention also provides a composition for treating diabetes comprising the insulin analogue or the insulin analogue derivative.

The present invention also provides a method for treating diabetes comprising a step of administering the insulin analogue or the insulin analogue derivative to a subject to need a blood glucose control.

The present invention also provides the insulin analogue or the insulin analogue derivative for use in the treatment of diabetes.

The present invention also provides a use of the insulin analogue or the insulin analogue derivative for the manufacture of a medicine for treating diabetes.

The present invention also provides a method for producing an active form of a long-acting insulin analogue derivative having an increased in vivo half-life, the method comprising the steps of: (a) culturing the recombinant microorganism; (b) lysing the cultured recombinant microorganism, thereby obtaining a long-acting insulin analogue derivative; (c) inducing refolding of the obtained long-acting insulin analogue derivative, thereby obtaining a pre-pro form of an insulin analogue derivative; (d) converting the pre-pro form of the insulin analogue derivative to an active form by treating with clostripain and CpB; and (e) purifying the active form of the long-acting insulin analogue derivative.

EXAMPLES

Hereinafter, the present invention will be described in further detail with reference to examples. It will be obvious to a person having ordinary skill in the art that these examples are for illustrative purposes only and are not to be construed to limit the scope of the present invention.

In examples below, an ABD-fused insulin analogue is used as the same meaning as that of the long-acting insulin analogue derivative in the present invention.

Example 1: Construction of ABD-Fused Insulin Expression Vector and Strain

Human insulin is synthesized as a form of pre-pro-insulin, the pre sequence is cleaved off in the endoplasmic reticulum, and the pro-insulin is processed in the Golgi body and the endoplasmic reticulum, thereby forming mature insulin. Based on this fact, in order to produce recombinant insulin by a process of expressing pro-insulin protein in *E. coli* and then removing the C-chain by trypsin treatment, pro-insulin was designed. In order to increase the efficiency of expression of pro-insulin in *E. coli* and the efficiency of purification, a fusion tag was inserted into the N-terminus, and codon optimization was performed.

The number of insulin sites to which an albumin-binding domain (ABD) may be fused is theoretically four. However, the N-terminus of the A-chain is a position important for the activity of insulin, and thus was excluded from the fusion positions. Although the N-terminus of the B-chain is important for the formation of an insulin hexamer, it was included in the fusion positions, because the activity of insulin could be maintained. If ABD is fused between B-chain and C-chain, it may have an effect on protein folding. Thus, the insulin construct was designed in either B-C-A order or A-C-B order as a candidate structure. Finally, gene structures for expression of the following three forms of ABD-fused insulin were designed:

NdeI-Fusion tag-B-chain-C-chain-A-chain-Linker-ABD-EcoRI,

NdeI-Fusion tag-ABD-Linker-B-chain-C-chain-A-chain-EcoRI, and

NdeI-Fusion tag-A-chain-C-chain-B-chain-Linker-ABD-EcoRI.

As an expression vector, a pJ401(DNA 2.0) vector was used. The vector was digested with the restriction enzymes NdeI and EcoRI, and then the DNA fragments were separated by electrophoresis on 1% agarose gel. The gene structures for expression of ABD fusion proteins and the DNA fragments obtained from the expression vector as described above were ligated to each other using T4 DNA ligase, thereby constructing plasmids. Next, each of the plasmids was transformed into *E. coli* BL21(DE3) by a calcium chloride method. Transformed strains having resistance to kanamycin were selected, and DNA was isolated therefrom. Whether the DNA would be properly inserted was determined by an analysis method based on restriction enzyme digestion.

When the gene was designed to have an NdeI-fusion tag-ABD-Linker-B-chain-C-chain-A-chain-EcoRI structure, it was determined not proper due to a very low protein refolding yield. In addition, when the gene was designed to have an NdeI-fusion tag-A-chain-C-chain-B-chain-Linker-ABD-EcoRI structure, the ABD-fused insulin had insulin activity, but it showed low refolding yield and enzyme treatment yield, thus it was deemed unsuitable as a method to make an active form of insulin. Therefore, among the three forms of ABD-fused insulin, the NdeI-fusion tag-B-chain-C-chain-A-chain-Linker-ABD-EcoRI structure was selected and used in a subsequent experiment.

Between the A-chain and the albumin-binding domain (ABD), a linker consisting of 1 to 6 repeats of a (GGGGS) sequence was inserted. In this case, when the linker was not introduced, the refolding yield was very low, but when a linker consisting of two or more repeats of the (GGGGS) sequence (SEQ ID NO: 16), there was not a significant difference in the refolding yield. Meanwhile, as n in the (GGGGS)$_n$ sequence (SEQ ID NO: 16) increased, the rate of conversion to an active form of insulin by clostripain increased, but the in vivo pharmacokinetics of the insulin were not significantly influenced. Taking the above-described results together, the linker was designed to consist of 2 to 4 repeats of the GGGGS sequence (SEQ ID NO: 16).

The amino acid sequences of each portions for the ABD-fused insulin used in the present invention are shown in Table 1 below.

TABLE 1

| | Sequence | Sequence ID No. |
|---|---|---|
| Fusion Tag | MATTSTGNSAHHHHHHSSGSAR | 1 |
| B chain | FVNQHLCGSHLVEALYLVCGEKGFFYTPKT | 2 |
| C chain | RREAEDLQVGQVELGGGPGAGSLQPLALEGSLQAR | 3 |
| A chain | GIVEQCCTSICSLYQLENYCN | 4 |
| Linker | GGGGSGGGGS | 5 |
| ABD | LAEAKEAANAELDSYGVSDFYKKLIDKAKTVEGVE ALKDAILAALP | 6 |

Example 2: Construction of ABD-Fused Insulin Analogues Having Modified Insulin Amino Acid Sequences To produce insulin using recombinant *E. coli*, a process of converting pro-insulin to an active form by use of trypsin is necessary. However, trypsin cleaves di-basic amino acids with high efficiency and also cleaves single amino acids such as lysine (Lys) or arginine (Arg), making it difficult to produce the desired active form of insulin. In addition, the ABD sequence also includes a number of lysine (Lys) and arginine (Arg) residues, making it further difficult to produce desired ABD-fused insulin having activity by use of trypsin.

For this reason, clostripain was used as an enzyme capable of replacing trypsin in order to induce conversion to an active form. In this case, when clostripain reacted with ABD-fused insulin, cleavage of arginine (Arg) at position 22 of the insulin B-chain occurred. To solve this problem, arginine (Arg) at position 22 of the B-chain was substituted with lysine (Lys). In this case, the cleavage at position 22 of the insulin B-chain by clostripain significantly decreased, and thus an active form of ABD-fused insulin could be effectively produced (FIG. 1).

In addition to the mutation as described above, additional mutations were introduced into the ABD-fused insulin in order to further increase the stability and in vivo half-life of the ABD-fused insulin. Five amino acids in each of the A-chain and the B-chain were substituted, and the substituted positions are shown in Table 2 below.

TABLE 2

| Analogue | Modified sequence |
|---|---|
| Analogue 1 | V→L at position 3 of A-chain |
| Analogue 2 | T→D at position 8 of A-chain |
| Analogue 3 | I→K at position 10 of A-chain |
| Analogue 4 | Y→E at position 14 of A-chain |
| Analogue 5 | Y→F at position 19 of A-chain |
| Analogue 6 | H→T at position 5 of B-chain |
| Analogue 7 | S→D at position 9 of B-chain |
| Analogue 8 | E→A at position 13 of B-chain |
| Analogue 9 | L→Q at position 17 of B-chain |
| Analogue 10 | F→S at position 24 of B-chain |
| Analogue 11 | No additional mutation in A-chain or B-chain |

Codon optimization for gene expression in *E. coli* was performed using the GeneArt algorithm, and genes were synthesized to have the substituted amino acids.

The plasmids constructed as described above were introduced into *E. coli* BL21(DE3) in the same manner as described in Example 1, thereby constructing *E. coli* strains.

Example 3: Expression of ABD-Fused Insulin Analogues

For expression of ABD-fused insulin analogues, each of the recombinant *E. coli* strains was inoculated into 100 mL of LB medium and shake-cultured at 37° C. for 16 hours, and the cultures were used as seed cultures. 2 L of LB medium was added to a 7-L fermenter (New Brunswick BioFlo), sterilized, and then inoculated with the seed culture. Culture was performed under the conditions of temperature of 35° C., air flow rate of 3 vvm and stirring speed of 1,000 rpm, and the pH during the culture was maintained at 6.8 with ammonia and phosphoric acid. At the time point at which the carbon source in the medium was exhausted, feeding was started and at the same time, protein expression was induced with IPTG. Additional culture was performed for 10 hours after induction of the expression, and recombinant strains were recovered using a centrifuge.

Figure 2:
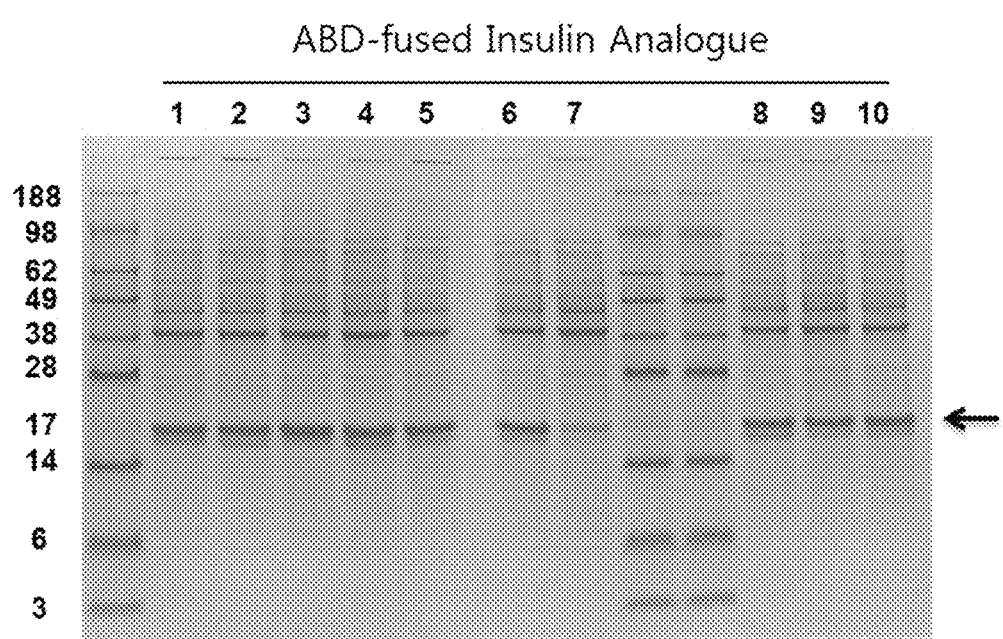
FIG. 2 shows the results of analyzing expression of ABD-fused insulin analogue derivatives 1 to 10 in recombinant *E. coli* by SDS-PAGE. Even when one or more mutations were introduced into the insulin sequence, protein expression in *E. coli* was retained.

The ABD-fused insulin analogues were expressed as inclusion bodies in the *E. coli* strain, and even when the amino acid mutations were introduced into the insulin domains, expression levels appeared in the vector system used in the present invention (FIG. 2).

Example 4: Induction of Cell Lysis and Solubilization/Refolding

Each of the strains expressing the ABD-fused insulin or the ABD-fused insulin analogues was suspended in lysis buffer (20 mM Tris, 10 mM EDTA, 10% sucrose, 0.2 M NaCl, pH 8.0), and the cells were lysed using a high-pressure homogenizer. The lysed cells were centrifuged in a high-speed centrifuge at 7,000 rpm, and soluble protein and some cell debris were removed, thereby isolating a precipitate including an inclusion body. The isolated inclusion body was washed with buffer (containing 1% Triton X-100, 0.2 M NaCl, and 1 M urea), and then centrifuged at 7,000 rpm. The precipitated inclusion body was additionally washed twice with distilled water, and was then stored at −80° C. until use.

Figure 3:
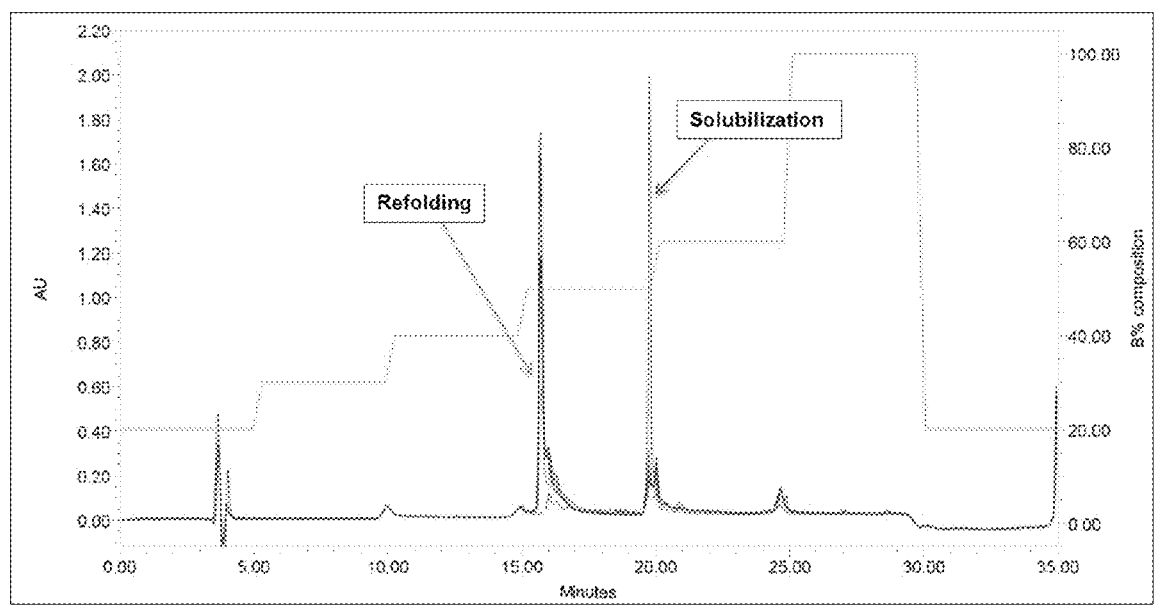
FIG. 3 shows the results of monitoring the solubilization and refolding of ABD-fused insulin analogue 4 by RP-HPLC. When the protein structure was unfolded by solubilization and followed by induction of refolding, the shift of retention time in RP-HPLC was observed due to formation of a three-dimensional structure.

The freeze-stored inclusion body was dissolved in solubilization buffer (25 mM Tris, 8 M Urea, 30 mM cysteine-HCl, pH 10.5), and then diluted in refolding buffer (25 mM Tris-HCl, pH 10.5), and subjected to refolding at 4° C. for 16 hours. Whether refolding would occur was determined by RP-HPLC analysis. When the solubilized solution was analyzed by RP-HPLC, the protein peak was observed at about 20 minutes due to high hydrophobicity, but when refolding proceeded, the shift of the peak to 16 minutes was observed (FIG. 3). This is because as the refolding progresses, the hydrophobicity decreases compared to that in the solubilized solution. The refolding was proceeded until the shift of the protein peak is not observed any more during the analysis by RP-HPLC.

Example 5: Conversion to Active Form by Use of Enzyme

For the production of insulin using a recombinant *E. coli* strain, the conversion of pro-insulin to an active form by use of trypsin is required. However, the ABD-fused insulin or the ABD-fused insulin analogue has a number of trypsin cleavage sites in its sequence, and for this reason, clostripain was used as an enzyme capable of replacing trypsin in order to induce conversion to an active form.

When conversion to an active form was induced using clostripain, cleavage at position 22 of the insulin B-chain occurred, making it difficult to produce a desired form of insulin. For this reason, an ABD-fused insulin analogue obtained by substituting position 22 of the B-chain from arginine (Arg) to lysine (Lys) was used to produce an active form of insulin.

Clostripain contains cysteine (Cys) in its active site, and thus requires reducing conditions in order to exhibit enzymatic activity. In addition, where a refolding solution is treated with a reducing agent in order to maintain clostripain activity, the disulfide bond in the insulin region is highly likely to be broken. For this reason, it is required to derive conditions that increase the enzymatic reaction yield without breaking the disulfide bond. Thus, using the reducing agent DTT contained in an enzymatic reaction solution, experiment was performed.

Because clostripain exists as a pro-form, auto-cleavage was induced to activate it. To this end, freeze-dried clostripain (Worthington, USA) was dissolved in distilled water, and then activated at 4° C. for 30 minutes after addition of activation buffer (500 mM Tris, 50 mM DTT, 25 mM CaCl$_2$ pH 7.8). The activated clostripain was added to the refolded protein at a concentration of 0.1 to 5 units per mg of the protein and allowed to react at 25 to 40° C. for 2 to 8 hours. After the clostripain reaction, CpB was added at a concentration of 0.001 to 1 unit per 1 mg of the protein and allowed to react. The enzymatic reaction was stopped by lowering the pH to 3.5 or less by use of HCl.

Figure 4:
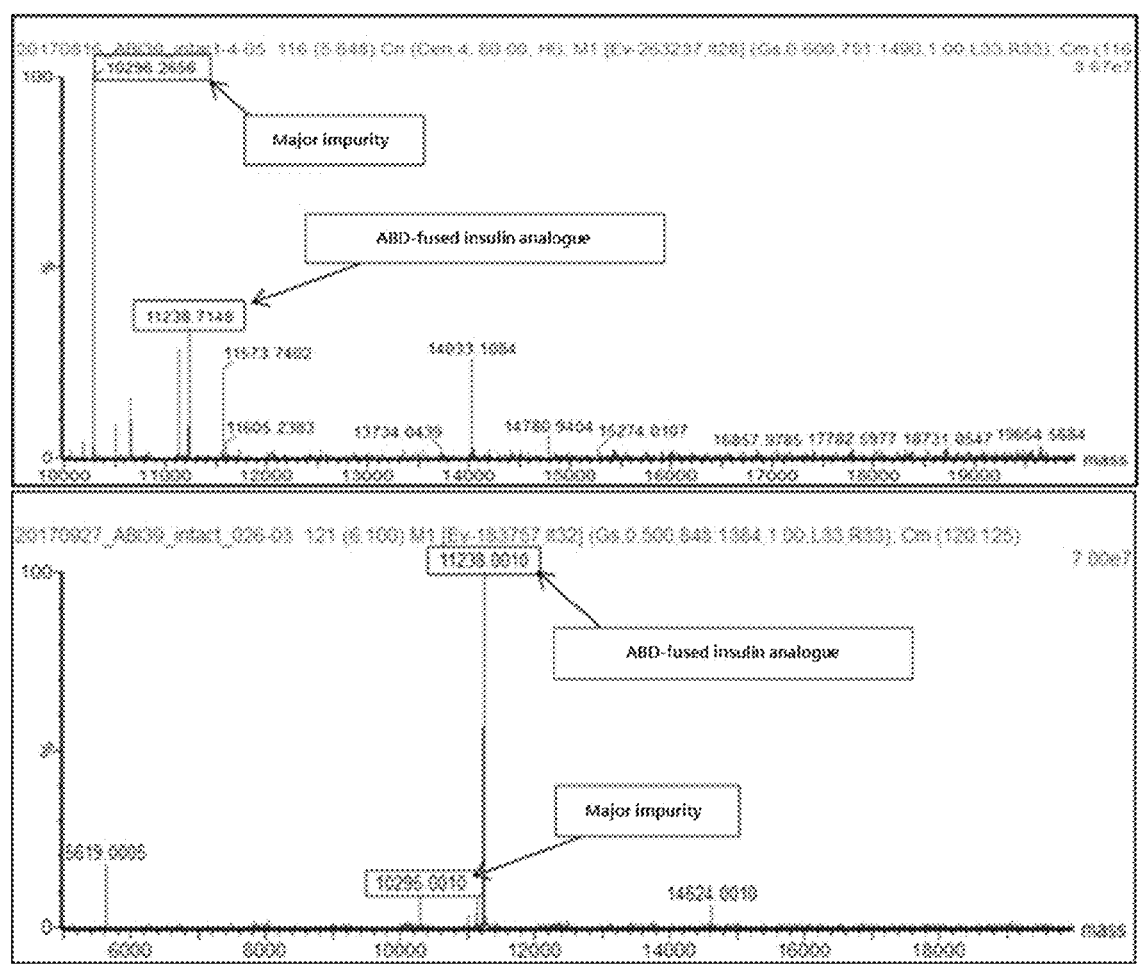
FIG. 4 shows the results obtained by performing an enzymatic reaction according to an example of the present invention and confirming the effects of increasing the efficiency of conversion to an active form of insulin and reducing impurities (molecular weight of major impurity: 10296 Da; molecular weight of active form of insulin: 11238 Da).

As a result, as can be seen in FIG. 4, the enzymatic reaction showed the effects of increasing the efficiency of conversion to an active form of insulin and reducing impurities.

Example 6: Purification of ABD-Fused Insulin

The sample enzymatically treated with clostripain and CpB was first purified by ion-exchange resin chromatography using Fractogel® EMD COO$^-$ (M) (Merck) according to its manufacturer's instruction, and then further purified by reverse-phase chromatography using Pharmprep® P100 RP-18e (Merck) according to its manufacturer's instruction.

Figure 5:
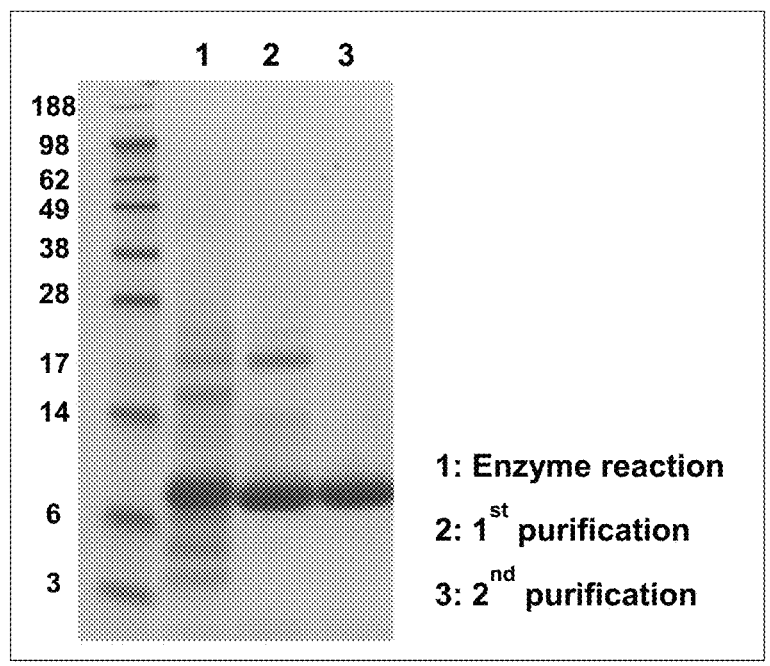
FIG. 5 shows the results of analyzing ABD-fused insulin analogue 4 by SDS-PAGE after digesting the insulin with clostripain and CpB and purifying it.

As a result, as can be seen in FIG. 5, an active form of impurity-free ABD-fused insulin could be purified by the two purification processes.

Example 7: Measurement of the Binding Affinities of ABD-Fused Insulin Analogues for Albumin To measure the binding affinities of the ABD-fused insulin analogue proteins for albumin, a surface plasmon resonance (SPR, BIACORE 3000, GE healthcare) analysis method was used. Recombinant human serum albumin was immobilized on a CM5 chip by an amine coupling method, and the ABD or ABD-fused insulin analogues diluted to five or more concentrations were bound thereto, and the affinities thereof for the human serum albumin were measured.

As a result, as can be seen in Table 3 below, the affinities of the insulin analogues for the human serum albumin were maintained at pM levels, even though they were lower than that of the ABD itself.

TABLE 3

| Analogue | $K_a$ (1/Ms) | $K_d$ (1/s) | $K_D$ (M) |
| --- | --- | --- | --- |
| Analogue 1 | $4.54 \times 10^5$ | $2.37 \times 10^{-5}$ | $5.21 \times 10^{-11}$ |
| Analogue 2 | $4.42 \times 10^5$ | $3.14 \times 10^{-5}$ | $7.11 \times 10^{-11}$ |
| Analogue 3 | $2.51 \times 10^5$ | $4.36 \times 10^{-5}$ | $1.74 \times 10^{-10}$ |
| Analogue 4 | $4.64 \times 10^5$ | $3.32 \times 10^{-5}$ | $7.17 \times 10^{-11}$ |
| Analogue 5 | $3.26 \times 10^5$ | $3.13 \times 10^{-5}$ | $9.6 \times 10^{-11}$ |
| Analogue 6 | $3.27 \times 10^5$ | $4.75 \times 10^{-5}$ | $1.45 \times 10^{-10}$ |
| Analogue 7 | $7.87 \times 10^5$ | $5.26 \times 10^{-5}$ | $6.68 \times 10^{-11}$ |
| Analogue 8 | $3.7 \times 10^5$ | $6.46 \times 10^{-5}$ | $1.75 \times 10^{-10}$ |
| Analogue 9 | $4.77 \times 10^5$ | $3.76 \times 10^{-5}$ | $7.9 \times 10^{-11}$ |
| Analogue 10 | $6.25 \times 10^5$ | $4.23 \times 10^{-5}$ | $6.77 \times 10^{-11}$ |
| ABD | $5.93 \times 10^6$ | $2.41 \times 10^{-5}$ | $7.29 \times 10^{-12}$ |

Example 8: Comparison of the Affinities of Native Insulin and ABD-Fused Insulin Analogues for Insulin Receptor To measure the binding affinities of native insulin and ABD-fused insulin analogues for insulin receptor, a surface plasmon resonance (SPR, BIACORE 3000, GE healthcare) analysis method was used. Insulin receptor was immobilized on a CM5 chip by an amine coupling method, and each of native insulin and ABD-fused insulin analogues, diluted to five or more concentrations, was bound thereto, and the affinities thereof for the insulin receptor were measured.

As a result, as can be seen in Table 4 below, the affinities of the ABD-fused insulin analogues were reduced compared to that of native insulin. In particular, the affinity of analogue 3 showed the greatest reduction and fell to a level of 19.4% relative to native insulin.

TABLE 4

| Analogue | $K_a$ (1/Ms) | $K_d$ (1/s) | $K_D$ (M) |
| --- | --- | --- | --- |
| Analogue 1 | $8.54 \times 10^4$ | — | — |
| Analogue 2 | $4.38 \times 10^4$ | $3.15 \times 10^{-3}$ | $7.2 \times 10^{-8}$ |
| Analogue 3 | $2.52 \times 10^4$ | $2.18 \times 10^{-3}$ | $8.65 \times 10^{-8}$ |
| Analogue 4 | $2.82 \times 10^4$ | $1.31 \times 10^{-3}$ | $4.65 \times 10^{-8}$ |
| Analogue 5 | $4.07 \times 10^4$ | $2.34 \times 10^{-3}$ | $5.75 \times 10^{-8}$ |
| Analogue 6 | $5.23 \times 10^4$ | $2.27 \times 10^{-3}$ | $4.33 \times 10^{-8}$ |
| Analogue 7 | $5.05 \times 10^4$ | — | — |
| Analogue 8 | $4.86 \times 10^4$ | $1.47 \times 10^{-3}$ | $3.04 \times 10^{-8}$ |
| Analogue 9 | $2.13 \times 10^4$ | $1.29 \times 10^{-3}$ | $6.06 \times 10^{-8}$ |
| Analogue 10 | $3.83 \times 10^4$ | — | — |
| Insulin | $1.03 \times 10^5$ | $1.72 \times 10^{-3}$ | $1.68 \times 10^{-8}$ |

The efficacies of the ABD-fused insulin analogues were evaluated comparatively with that of insulin glargine in type 1 diabetic models induced by streptozotocin. Analogues 1, 3 and 10 were excluded from candidates since they showed a blood glucose lowering ability of 50% or less compared to insulin glargine.

Example 9: Hexamer Synthesis

Figure 6:
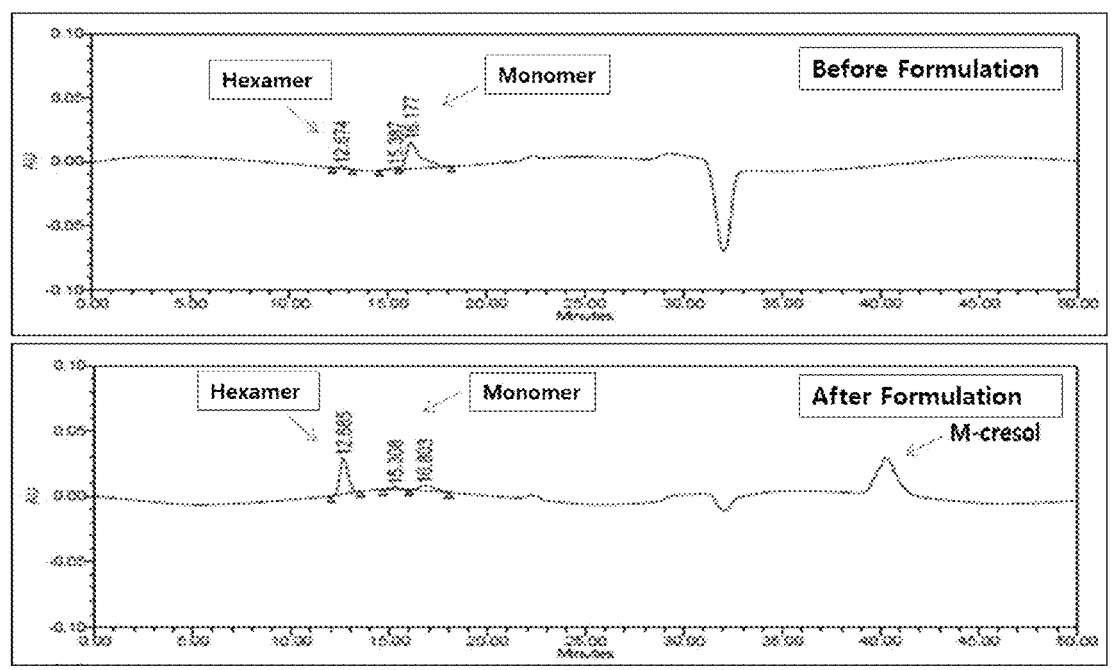
FIG. 6 shows the results of size-exclusion chromatography analysis performed to examine whether a hexamer would be formed when zinc and phenol were added to an ABD-fused insulin analogue according to an example of the present invention.

Insulin binds to zinc in vivo, thereby forming a stable hexamer structure. The insulin's property of forming a hexamer is also used in formulation development and may play an important role in increasing the in vivo half-life of insulin. Accordingly, whether the ABD-fused insulin analogues would retain the property of forming hexamers was analyzed by size-exclusion chromatography. As a result, it was shown that analogue 4 retained the ability to form a hexamer by addition of zinc and phenol (FIG. 6). The formation of the hexamer was also observed in all the analogues excluding analogues 7, 9 and 10. Thus, among the analogues having the sequences shown in Table 2, analogues 7 and 9 were further excluded from candidates.

Example 10: Evaluation of In Vivo Pharmacokinetics and Blood Glucose Lowering Ability of ABD-Fused Insulin Analogues To evaluate the in vivo pharmacokinetics of the six ABD-fused insulin analogues, each of the insulin analogues was administered subcutaneously to normal SD rats (6-week old), and then blood was sampled at 0, 1, 4, 8, 24, 48, 72 and 96 hours. The concentration of each ABD-fused insulin analogue remaining in the blood at each of the time points was measured using ELISA. In addition, using a portion of the sampled blood, time-dependent blood glucose levels were measured with a blood glucose monitoring device.

As a result, as can be seen in Table 5 below, the ABD-fused insulin analogues showed significantly increased half-lives compared to native insulin known to have a half-life of 5 minutes. Analogue 11 obtained by substituting only position 22 of the insulin B-chain showed a half-life of 7.2 hours, and analogue 4 showing the greatest increase in half-life was evaluated to have a half-life of 9.9 hours.

Figure 7:
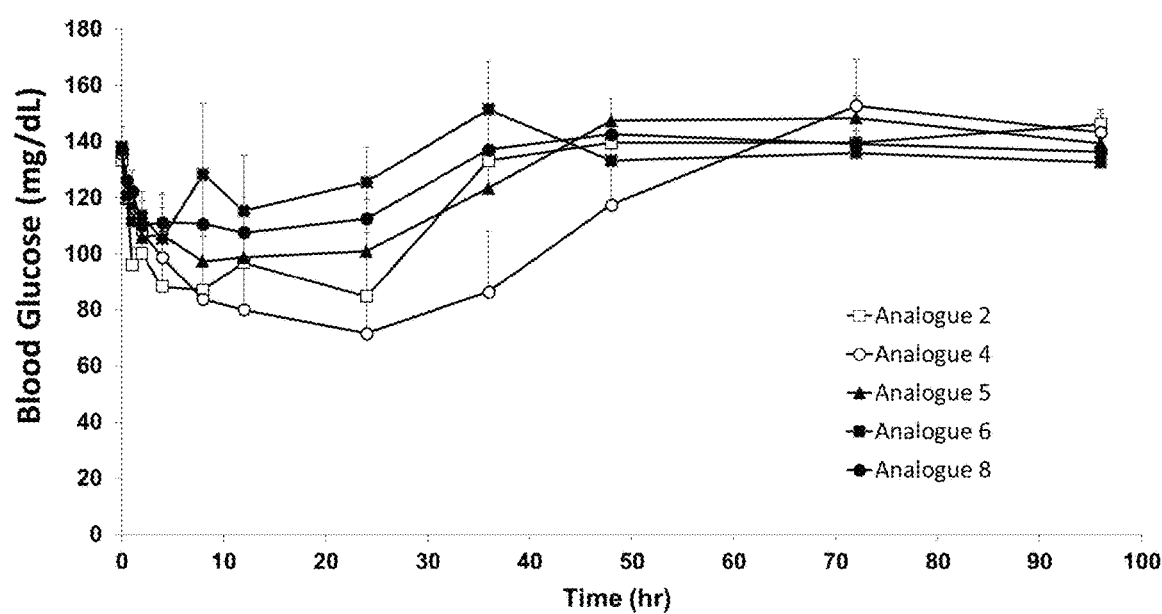
FIG. 7 shows the results of evaluating the blood glucose lowering ability of ABD-fused insulin analogues according to an example of the present invention.

The time during which blood glucose levels in the normal animals were maintained at reduced levels was analyzed. As a result, it was shown that analogues 5, 6 and 8 had increased half-lives, but maintained blood glucose levels for a short time. In comparison with these analogues, analogue 4 had the best ability to lower blood glucose levels and maintained its efficacy for the longest time (FIG. 7).

TABLE 5

| Parameter | Analogue 2 | Analogue 4 | Analogue 5 | Analogue 6 | Analogue 8 | Analogue 11 |
| --- | --- | --- | --- | --- | --- | --- |
| $T_{1/2}$ (hr) | 9.4 ± 3.4 | 9.9 ± 0.1 | 9.1 ± 0.7 | 8.4 ± 1.7 | 8.8 ± 0.4 | 7.2 ± 2.3 |
| MRT (hr) | 17.0 ± 2.2 | 22.1 ± 1.3 | 21.2 ± 0.3 | 15.9 ± 1.5 | 19.8 ± 1.5 | 16.3 ± 0.9 |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The insulin analogue or insulin analogue derivative according to the present invention has advantages over conventional insulin, insulin analogues or other insulin derivatives in that it has a significantly increased in vivo half-life and increased stability, so that it can have a long-lasting effect even when it is injected once. Thus, it can provide convenience to diabetic patients who self-administer insulin by injection.

The invention claimed is:

1. An insulin analogue comprising an insulin B-chain variant represented by the amino acid sequence of SEQ ID NO: 2, arginine (Arg) at amino acid position 22 of an insulin B-chain is substituted with lysine (Lys) in native insulin,
wherein the insulin analogue further comprises an amino acid substitution selected from the group consisting of:
a threonine (Thr)-to-aspartic acid (Asp) substitution at amino acid position 8 of the insulin A-chain represented by the amino acid sequence of SEQ ID NO: 4;
a tyrosine (Tyr)-to-glutamic acid (Glu) substitution at amino acid position 14 of the insulin A-chain represented by the amino acid sequence of SEQ ID NO: 4;
a tyrosine (Tyr)-to-phenylalanine (Phe) substitution at amino acid position 19 of the insulin A-chain represented by the amino acid sequence of SEQ ID NO: 4;
a histidine (His)-to-threonine (Thr) substitution at amino acid position 5 of an insulin B-chain variant represented by the amino acid sequence of SEQ ID NO: 2;
a serine (Ser)-to-aspartic acid (Asp) substitution at amino acid position 9 of the insulin B-chain variant represented by the amino acid sequence of SEQ ID NO: 2;
a glutamic acid (Glu)-to-alanine (Ala) substitution at amino acid position 13 of the insulin B-chain variant represented by the amino acid sequence of SEQ ID NO: 2; and
a leucine (Leu)-to-glutamine (Gln) substitution at amino acid position 17 of the insulin B-chain variant represented by the amino acid sequence of SEQ ID NO: 2.

2. The insulin analogue of claim 1, wherein the insulin analogue shows a resistance to cleavage by enzyme clostripain.

3. The insulin analogue of claim 1, wherein the insulin analogue has an increased in vivo half-life compared to native insulin.

4. A polynucleotide encoding the insulin analogue of claim 1.

5. A recombinant vector comprising the polynucleotide of claim 4.

6. A recombinant microorganism having introduced therein the recombinant vector of claim 5.

7. A long-acting insulin analogue derivative in which an albumin-binding domain is fused to the insulin analogue of claim 1.

8. The long-acting insulin analogue derivative of claim 7, wherein the albumin-binding domain comprises an albumin-binding motif represented by the following amino acid sequence:

```
GVSDFYKKLIX_aKAKTVEGVEALKX_bX_cI  (SEQ ID NO: 14)
```

Wherein
$X_a$ is independently selected from D and E,
$X_b$ is independently selected from D and E, and
$X_c$ is independently selected from A and E.

9. The long-acting insulin analogue derivative of claim 8, wherein the albumin-binding domain comprises the following amino acid sequence:

```
LAX_3AKX_6X_7ANX_10ELDX_14Y-[BM]-LX_43X_44LP  (SEQ ID NO: 15)
``` wherein
[BM] is the albumin-binding motif as defined in claim 8 (SEQ ID NO: 14),
$X_3$ is independently selected from C, E, Q, and S;
$X_6$ is independently selected from C, E, and S;
$X_7$ is independently selected from A and S;
$X_{10}$ is independently selected from A, R, and S;
$X_{14}$ is independently selected from A, C, K, and S;
$X_{43}$ is independently selected from A and K; and
$X_{44}$ is independently selected from A, E, and S.

10. The long-acting insulin analogue derivative of claim 9, wherein the albumin-binding domain is represented by an amino acid sequence selected from the group consisting of SEQ ID NOS: 6 to 13.

11. The long-acting insulin analogue derivative of claim 10, wherein the albumin-binding domain is represented by the amino acid sequence of SEQ ID NO: 6.

12. The long-acting insulin analogue derivative of claim 7, wherein the insulin analogue and the albumin-binding domain are linked to each other by a peptide bond; a polypeptide linker; or a non-peptidyl linker selected from the group consisting of polyethylene glycol, polypropylene glycol, an ethylene glycol-propylene glycol copolymer, polyoxyethylated polyol, polyvinyl alcohol, polysaccharides, dextran, polyvinyl ethyl ether, biodegradable polymers, fatty acids, nucleotides, lipid polymers, chitin, hyaluronic acid, and combinations thereof.

13. The long-acting insulin analogue derivative of claim 12, wherein the polypeptide linker is (GGGGS)$_n$ wherein n=an integer ranging from 1 to 6 (SEQ ID NO: 16).

14. The long-acting insulin analogue derivative of claim 13, wherein the polypeptide linker is represented by the amino acid sequence of SEQ ID NO: 5.

15. A recombinant vector that comprises: a polynucleotide of claim 4; and a polynucleotide encoding an albumin-binding domain comprising an albumin-binding motif represented by the following amino acid sequence:

```
GVSDFYKKLIX_aKAKTVEGVEALKX_bX_cI  (SEQ ID NO: 14)
``` wherein
$X_a$ is independently selected from D and E,
$X_b$ is independently selected from D and E, and
$X_c$ is independently selected from A and E.

16. The recombinant vector of claim 15, wherein the albumin-binding domain comprises the following amino acid sequence:

```
LAX_3AKX_6X_7ANX_10ELDX_14Y-[BM]-LX_43X_44LP  (SEQ ID NO: 15)
```

Wherein
[BM] is the albumin-binding motif as defined in claim 15 (SEQ ID NO: 14),
$X_3$ is independently selected from C, E, Q, and S;
$X_6$ is independently selected from C, E, and S;
$X_7$ is independently selected from A and S;
$X_{10}$ is independently selected from A, R, and S;
$X_{14}$ is independently selected from A, C, K, and S;
$X_{43}$ is independently selected from A and K; and
$X_{44}$ is independently selected from A, E, and S.

17. The recombinant vector of claim 16, wherein the albumin-binding domain is represented by an amino acid sequence selected from the group consisting of SEQ ID NOS: 6 to 13.

18. The recombinant vector of claim 17, wherein the albumin-binding domain is represented by the amino acid sequence of SEQ ID NO: 6.

19. A recombinant microorganism having introduced therein the recombinant vector of claim 15.

20. A method for producing an active form of a long-acting insulin analogue derivative having an increased in vivo half-life, the method comprising the steps of:
(a) culturing the recombinant microorganism of claim 19;
(b) lysing the cultured recombinant microorganism, thereby obtaining a long-acting insulin analogue derivative;
(c) inducing refolding of the obtained long-acting insulin analogue derivative, thereby obtaining a pre-pro form of an insulin analogue derivative;
(d) converting the pre-pro form of the insulin analogue derivative to an active form by treating with clostripain and CpB; and
(e) purifying the active form of the long-acting insulin analogue derivative.

* * * * *

SEQUENCE LISTING

<160> NUMBER OF SEQ ID NOS: 16

<210> SEQ ID NO 1
<211> LENGTH: 22
<212> TYPE: PRT
<213> ORGANISM: Artificial Sequence
<220> FEATURE:
<223> OTHER INFORMATION: Synthetic construct

<400> SEQUENCE: 1

Met Ala Thr Thr Ser Thr Gly Asn Ser Ala His His His His His
1               5                   10                  15

Ser Ser Gly Ser Ala Arg
            20

<210> SEQ ID NO 2
<211> LENGTH: 30
<212> TYPE: PRT
<213> ORGANISM: Artificial Sequence
<220> FEATURE:
<223> OTHER INFORMATION: Synthetic construct

<400> SEQUENCE: 2

Phe Val Asn Gln His Leu Cys Gly Ser His Leu Val Glu Ala Leu Tyr
1               5                   10                  15

Leu Val Cys Gly Glu Lys Gly Phe Phe Tyr Thr Pro Lys Thr
            20                  25                  30

<210> SEQ ID NO 3
<211> LENGTH: 35
<212> TYPE: PRT
<213> ORGANISM: Artificial Sequence
<220> FEATURE:
<223> OTHER INFORMATION: Synthetic construct

<400> SEQUENCE: 3

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 4
<211> LENGTH: 21
<212> TYPE: PRT
<213> ORGANISM: Artificial Sequence
<220> FEATURE:
<223> OTHER INFORMATION: Synthetic construct

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 5

Gly Gly Gly Gly Ser Gly Gly Gly Gly Ser
1               5                   10

<210> SEQ ID NO 6
<211> LENGTH: 46
<212> TYPE: PRT
<213> ORGANISM: Artificial Sequence
<220> FEATURE:
<223> OTHER INFORMATION: Synthetic construct

<400> SEQUENCE: 6

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 7
<211> LENGTH: 46
<212> TYPE: PRT
<213> ORGANISM: Artificial Sequence
<220> FEATURE:
<223> OTHER INFORMATION: Synthetic construct

<400> SEQUENCE: 7

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 8
<211> LENGTH: 46
<212> TYPE: PRT
<213> ORGANISM: Artificial Sequence
<220> FEATURE:
<223> OTHER INFORMATION: Synthetic construct

<400> SEQUENCE: 8

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 9
<211> LENGTH: 46
<212> TYPE: PRT
<213> ORGANISM: Artificial Sequence
<220> FEATURE:
<223> OTHER INFORMATION: Synthetic construct

<400> SEQUENCE: 9

Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
            20                  25                  30
```

Gly Val Glu Ala Leu Lys Glu Glu Ile Leu Ala Ala Leu Pro
            35                  40                  45

<210> SEQ ID NO 10
<211> LENGTH: 46
<212> TYPE: PRT
<213> ORGANISM: Artificial Sequence
<220> FEATURE:
<223> OTHER INFORMATION: Synthetic construct

<400> SEQUENCE: 10

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 11
<211> LENGTH: 46
<212> TYPE: PRT
<213> ORGANISM: Artificial Sequence
<220> FEATURE:
<223> OTHER INFORMATION: Synthetic construct

<400> SEQUENCE: 11

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
                20                  25                  30

Gly Val Glu Ala Leu Lys Asp Glu Ile Leu Ala Ala Leu Pro
            35                  40                  45

<210> SEQ ID NO 12
<211> LENGTH: 46
<212> TYPE: PRT
<213> ORGANISM: Artificial Sequence
<220> FEATURE:
<223> OTHER INFORMATION: Synthetic construct

<400> SEQUENCE: 12

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
                20                  25                  30

Gly Val Glu Ala Leu Lys Glu Ala Ile Leu Ala Ala Leu Pro
            35                  40                  45

<210> SEQ ID NO 13
<211> LENGTH: 46
<212> TYPE: PRT
<213> ORGANISM: Artificial Sequence
<220> FEATURE:
<223> OTHER INFORMATION: Synthetic construct

<400> SEQUENCE: 13

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
                20                  25                  30

Gly Val Glu Ala Leu Lys Glu Glu Ile Leu Ala Ala Leu Pro
            35                  40                  45

```
<210> SEQ ID NO 14
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa is independently selected from Asp and Glu
<220> FEATURE:
<221> NAME/KEY: MISC_FEATURE
<222> LOCATION: (24)..(24)
<223> OTHER INFORMATION: Xaa is independently selected from Asp and Glu
<220> FEATURE:
<221> NAME/KEY: MISC_FEATURE
<222> LOCATION: (25)..(25)
<223> OTHER INFORMATION: Xaa is independently selected from Ala and Glu

<400> SEQUENCE: 14

Gly Val Ser Asp Phe Tyr Lys Lys Leu Ile Xaa Lys Ala Lys Thr Val
1               5                   10                  15

Glu Gly Val Glu Ala Leu Lys Xaa Xaa Ile
            20                  25

<210> SEQ ID NO 15
<211> LENGTH: 46
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is independently selected from Cys, Glu,
      Gln, and Ser
<220> FEATURE:
<221> NAME/KEY: MISC_FEATURE
<222> LOCATION: (6)..(6)
<223> OTHER INFORMATION: Xaa is independently selected from Cys, Glu,
      and Ser
<220> FEATURE:
<221> NAME/KEY: MISC_FEATURE
<222> LOCATION: (7)..(7)
<223> OTHER INFORMATION: Xaa is independently selected from Ala and Ser
<220> FEATURE:
<221> NAME/KEY: MISC_FEATURE
<222> LOCATION: (10)..(10)
<223> OTHER INFORMATION: Xaa is independently selected from Ala, Arg,
      and Ser
<220> FEATURE:
<221> NAME/KEY: MISC_FEATURE
<222> LOCATION: (14)..(14)
<223> OTHER INFORMATION: Xaa is independently selected from Ala, Cys,
      Lys, and Ser
<220> FEATURE:
<221> NAME/KEY: MISC_FEATURE
<222> LOCATION: (26)..(26)
<223> OTHER INFORMATION: Xaa is independently selected from Asp and Glu
<220> FEATURE:
<221> NAME/KEY: MISC_FEATURE
<222> LOCATION: (39)..(39)
<223> OTHER INFORMATION: Xaa is independently selected from Asp and Glu
<220> FEATURE:
<221> NAME/KEY: MISC_FEATURE
<222> LOCATION: (40)..(40)
<223> OTHER INFORMATION: Xaa is independently selected from Ala and Glu
<220> FEATURE:
<221> NAME/KEY: MISC_FEATURE
<222> LOCATION: (43)..(43)
<223> OTHER INFORMATION: Xaa is independently selected from Ala and Lys
<220> FEATURE:
<221> NAME/KEY: MISC_FEATURE
<222> LOCATION: (44)..(44)
```

```
<223> OTHER INFORMATION: Xaa is independently selected from Ala, Glu and
      Ser

<400> SEQUENCE: 15

Leu Ala Xaa Ala Lys Xaa Xaa Ala Asn Xaa Glu Leu Asp Xaa Tyr Gly
1               5                   10                  15

Val Ser Asp Phe Tyr Lys Lys Leu Ile Xaa Lys Ala Lys Thr Val Glu
            20                  25                  30

Gly Val Glu Ala Leu Lys Xaa Xaa Ile Leu Xaa Xaa Leu Pro
            35                  40                  45

<210> SEQ ID NO 16
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: REPEAT
<222> LOCATION: (1)..(5)
<223> OTHER INFORMATION: the number of repeats of the repeat unit is an
      integer of from 1 to 6

<400> SEQUENCE: 16

Gly Gly Gly Gly Ser
1               5
```